United States Patent [19]

Ducharme et al.

[11] Patent Number: 5,657,126
[45] Date of Patent: *Aug. 12, 1997

[54] ELLIPSOMETER

[75] Inventors: Stephen Paul Ducharme, Lincoln, Nebr.; Hassanayn Machlab El Hajj, Iowa City, Iowa; Blaine D. Johs; John A. Woollam, both of Lincoln, Nebr.

[73] Assignee: The Board of Regents of the University of Nebraska, Lincoln, Nebr.

[*] Notice: The term of this patent shall not extend beyond the expiration date of Pat. No. 5,416,588.

[21] Appl. No.: 440,715

[22] Filed: May 15, 1995

Related U.S. Application Data

[63] Continuation-in-part of Ser. No. 284,284, Aug. 2, 1994, Pat. No. 5,416,588, which is a continuation of Ser. No. 994,197, Dec. 21, 1992, abandoned.

[51] Int. Cl.$^6$ .................................................. G01N 21/21
[52] U.S. Cl. ............................................... 356/369; 250/225
[58] Field of Search ..................................... 356/364–370, 356/381, 382; 359/246, 249, 252, 278, 279, 281, 284–287; 250/225

[56] References Cited

U.S. PATENT DOCUMENTS

| | | | |
|---|---|---|---|
| 3,594,085 | 7/1971 | Wilmanns | 356/369 |
| 3,734,625 | 5/1973 | Aagard | 356/369 |
| 3,880,524 | 4/1975 | Dill et al. | 356/369 |
| 3,981,578 | 9/1976 | Gievers | 356/368 |
| 4,053,232 | 10/1977 | Dill et al. | 356/369 |
| 4,306,809 | 12/1981 | Azzam | 356/369 |
| 4,585,348 | 4/1986 | Chastang et al. | 356/369 |
| 4,872,758 | 10/1989 | Miyazaki et al. | 356/382 |
| 4,953,980 | 9/1990 | De Volk et al. | 356/367 |

OTHER PUBLICATIONS

J. Badoz, M. P. Silverman, and J. C. Canit, "Wave Propagation Through a Medium with Static and Dynamic Birefringence: Theory of the Photoelastic Modulator," Journal of the Optical Society of America A/vol. 7, No. 4/Apr. 1990, pp. 672–682.

F. A. Modine and G. E. Jellison, "Errors in Polarization Measurements Due to Static Retardation in Photoelastic Modulators," Applied Physics Communications, 12(1), 121–139 (1993).

V. M. Bermudez and V. H. Ritz, "Wavelength–scanning Polarization–modulation ellipsometry: some practical considerations" Applied Optics, vol. 17, No. 4/Feb. 15, 1978; pp. 542–552.

G. E. Jellison, Jr. and F. A. Modine, "Accurate calibration of a photo–elastic modulator in polarization modulation ellipsometry," Proceedings of the SPIE, vol. 1166 (SPIE, Bellingham, WA, 1990) pp. 231–241.

Primary Examiner—Hoa Q. Pham
Attorney, Agent, or Firm—Vincent L. Carney

[57] ABSTRACT

In an ellipsometer, a phase-modulated, polarized light beam is applied to a sample, electrical signals are obtained representing the orthogonal planes of polarization of the light after it has interacted with the sample and the constants of the sample are calculated from the two resulting electrical signals. The phase modulation is sufficiently small so that the calibration errors are negligible. For this purpose, the phase modulator, phase modulates the light within a range of no more than ten degrees peak to peak. The two electrical signals are expanded by Fourier analysis and the coefficients thereof utilized to calculate psi and delta.

10 Claims, 2 Drawing Sheets

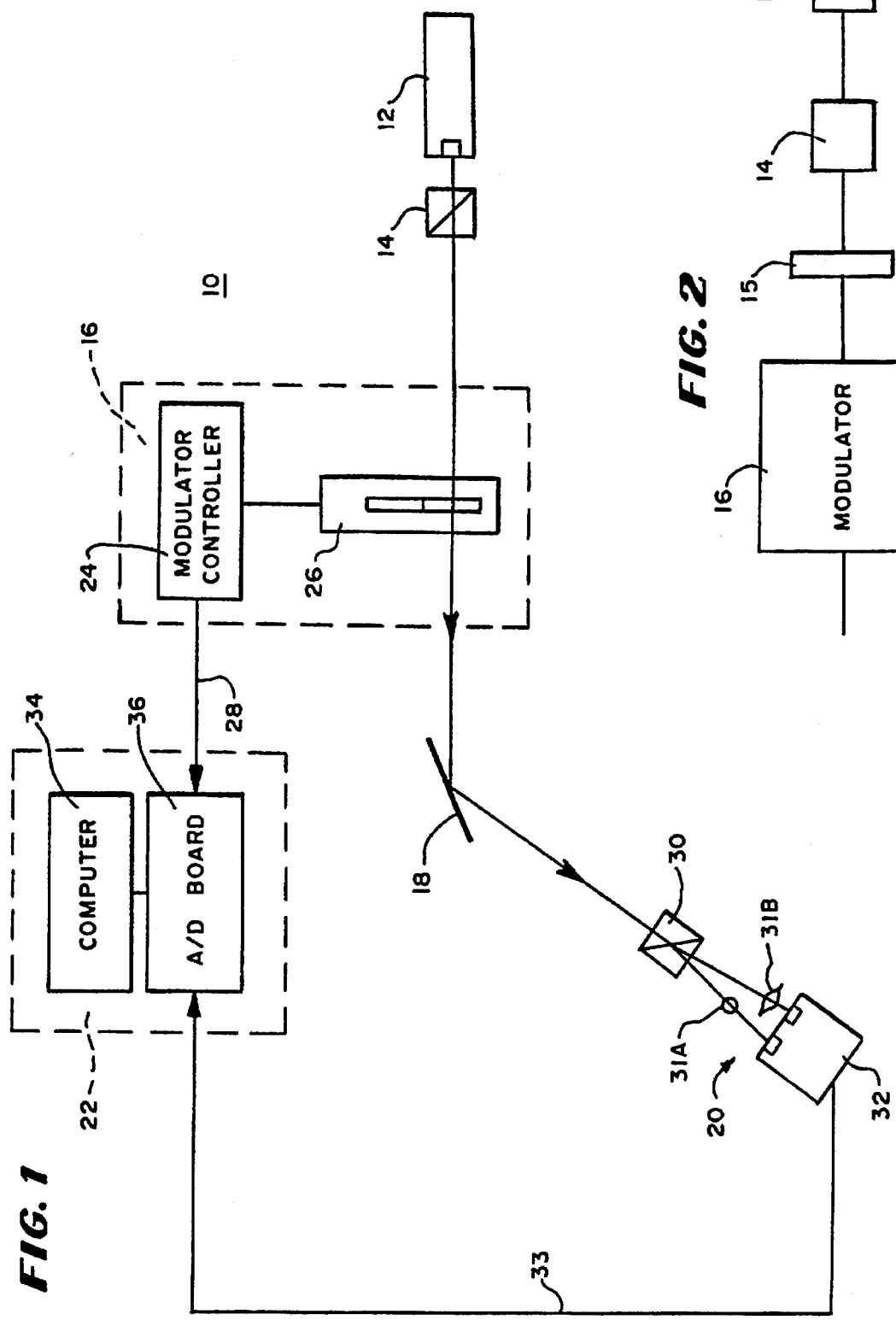

ELLIPSOMETER

RELATED APPLICATIONS

This application is a continuation-in-part patent application of U.S. patent application Ser. No. 08/284,284 (now U.S. Pat. No. 5,416,588) filed Aug. 2, 1994 which is a continuation of U.S. patent application Ser. No. 07/994,197 filed Dec. 21, 1992, entitled SMALL MODULATION ELLIPSOMETRY (now abandoned).

RIGHT IN THE UNITED STATES GOVERNMENT

This invention was made with Government support under contracts NAS8-39327 and NAS8-39920 awarded by NASA. The Government has certain rights in this invention.

BACKGROUND OF THE INVENTION

This invention relates to ellipsometry.

One class of ellipsometers includes a light source, a polarizer, a modulator, an analyzer and at least one intensity detector. In this class of ellipsometer, the light is modulated and sensed by a photocell. The resulting electric signal is used to calculate psi and delta, which can be done by a number of known techniques including a Fourier expansion of the resulting signal.

In this class of ellipsometry, errors occur, such as for example, because of Changes in angular rotational alignment or tilt of the modulator or polarizers or sample about the optical axis or changes in the environment that cause signals to be processed in a nonlinear portion of the components of the instrument. Moreover in one type of ellipsometer in this class of ellipsometers, called a large modulation ellipsometer, the modulator varies the intensity of the beam over a defined range sufficiently large to give an easily measured signal to avoid poor signal to noise ratios.

Because of changes in the environment, corrections may need to be made such as in the software to make the necessary corrections or adjustment of voltages or adjustment of amplification level of amplifiers or sensors or attenuation levels of signals from photocells or changes in the angle of the diffraction grating if one is included or in the polarizer. For example, the photocell output signal in some ranges changes nonlinearly with respect to changes in the intensity of light and the light reflected from diffration gratings, if any are included, change nonlinearly with respect to changes in the phase. The changes in ranges of intensity and polarization state are caused by changes in reflected or transmitted light as the environment of measurement changes.

In a prior art type of ellipsometer in this class, these errors are corrected in a manner that requires time consuming calibration for different environments. The calibration of alignment is generally obtained by measuring the psi and delta of a known environment similar to the one being tested and calibrating the instrument in that known environment to provide correction factors. Only the first order and second order coefficients of the Fourier series are used in the prior art calculate delta and psi because these coefficients are known to contain sufficient information by themselves to calculate delta and psi.

This prior art type of ellipsometry has a disadvantage in that a large amount of time is necessary to correct the system by calibration and the instrument is limited in the benefits it can provide for some uses such as those in which the environment changes frequently. This disadvantage of prior art type of ellipsometers is especially severe when continuous measurements of time varying quantities are made because of the need to calibrate for different surfaces.

SUMMARY OF THE INVENTION

Accordingly, it is an object of the invention to provide a novel ellipsometry technique.

It is a still further object of the invention to provide a novel ellipsometer capable of measuring time varying changes in surfaces in real time.

It is a still further object of the invention to provide a novel ellipsometric technique which does not require calibration when measuring time varying surfaces over a wide range.

It is a still further object of the invention to provide an ellipsometric technique and instrument in which the calibration constants do not require frequent adjustment.

It is a still further object of the invention to utilize information in one or both of the third and fourth order coefficients of a Fourier series to correct data for misalignment of the analyzer or modulator.

It is a still further object of this invention to provide an amplitude modulation ellipsometer which provides values of the modulation or amplitude and two channel calibration factors without external calibration.

It is a still further object of the invention to provide values of psi and delta for a specimen using zero through fourth order coefficients of a Fourier series.

It is a still further object of the invention to provide a novel on-line correction for alignment errors of the modulation, polarizer and sample due to rotation or tilt about the optical axis.

In accordance with the above and further objects of the invention, an ellipsometer includes a source of light, a polarizer, a modulator and a split analyzer. The sample receives polarized light from the source and reflects or transmits that light with a change in its polarization state. In one embodiment, the light is modulated with such value as to cause the calibration errors related to changes in the orientation of the polarized light and light intensity to be insignificant and in a second embodiment a larger modulation value is used to provide a better signal to noise ratio and the data is corrected for calibration errors using information in one or both of the third and fourth order coefficients of the Fourier transform.

A split analyzer: (1) separates the light reflected from or transmitted through the sample into two different mutually orthogonal components, each of which represents a linear combination of light, one mainly polarized in alignment with the "p" plane and the other mainly polarized in alignment with the "s" plane; (2) converts each component into a different electrical signal; (3) subjects the signals to Fourier analysis to obtain a Fourier series for each; and (4) calculates the values of delta and psi from the coefficients of the Fourier series using at least the values through the third order and preferably through the fourth order. Although the two components have mutually orthogonal polarization, the polarizations are not identical to the "s" and "p" polarizations relative to the sample. The separate electrical signals from two light beams are utilized to determine psi and delta and to correct data for misalignment errors.

The amount of modulation that renders the calibration constants insignificant is usually in the order of three or four degrees, but always under ten degrees and preferably under 5 degrees of phase modulation. The amount can be determined for specific environments from a Jones matrix by deciding on the degree of error that is tolerable and setting the angles of the sines and cosines below that amount for modulation. For the purpose of this specification, the amount of modulation is considered as the number of degrees of a complete wavelength of light. Amplitude modulation may also be used to reduce noise by synchronous detection.

In the second embodiment, the amount of modulation that improves accuracy may be larger than one-half radian to provide good signal to noise ratios. It is not necessary to use values more than two radians and some problems occur at specific larger values. Thus, in one embodiment, a phase modulator modulates the light at a value above one-half pi to correct for calibration errors. Moreover, there are mechanical limits to the magnitude of modulators possible. In the preferred embodiment the modulation is about one radian.

This ellipsometric technique has several advantages, such as: (1) it can measure a changing environment, such as for example a surface that is in use such as in a spacecraft or the like; and (2) there is less time necessary for calibrating the instrument to different surfaces.

DESCRIPTION OF THE DRAWINGS

The above noted and other features of the invention will be better understood from the following detailed description when considered with reference to the accompanying drawings, in which:

FIG. 1 is a block diagram of one embodiment of small modulation ellipsometer in accordance with the invention;

FIG. 2 is a fragmentary block diagrammatic view of a modification of the ellipsometer of FIG. 1 that forms a second embodiment.

DETAILED DESCRIPTION

Figure 3:
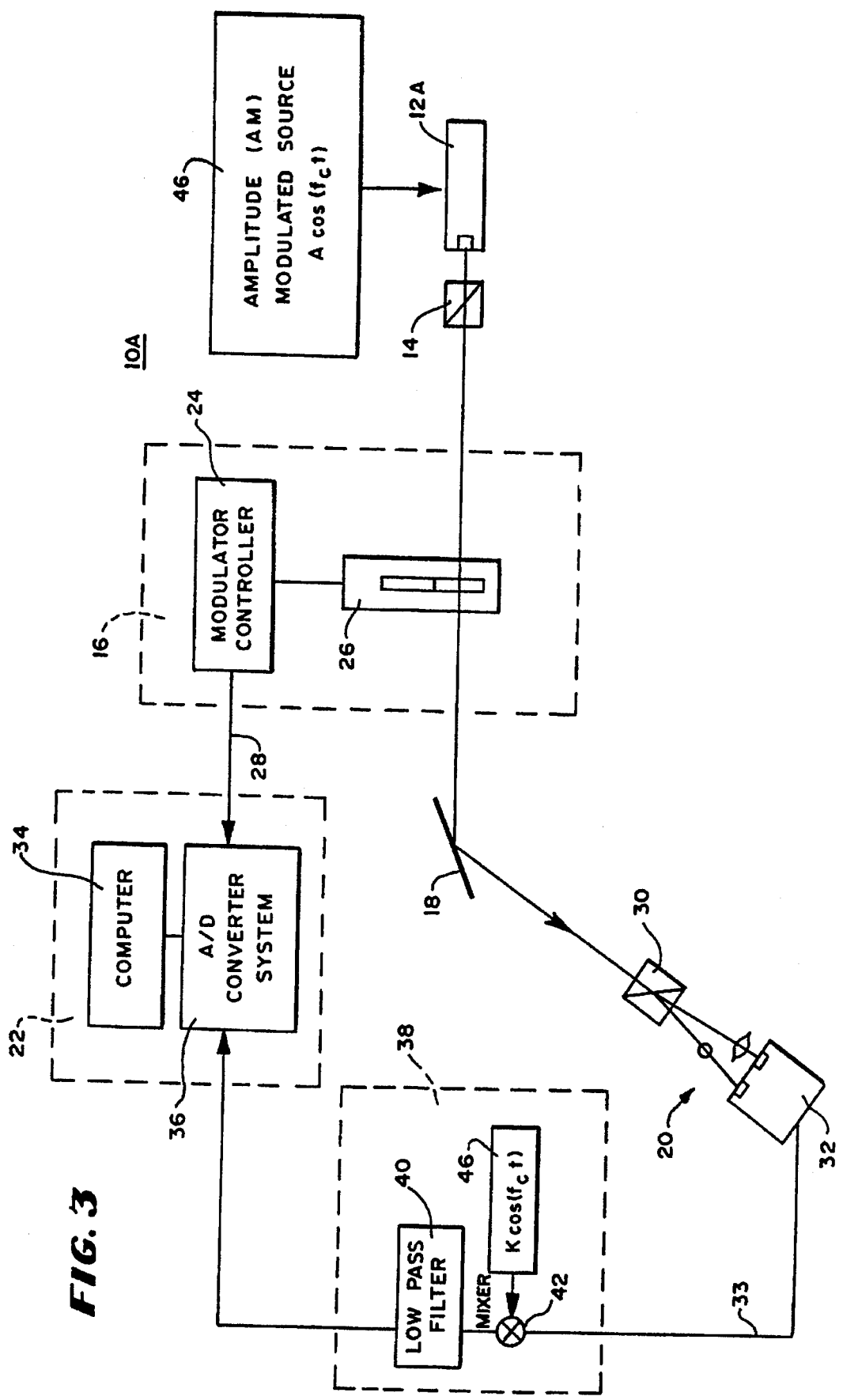
FIG. 3 is a block diagram of a third embodiment of ellipsometer in accordance with the invention.

In FIG. 1, there is shown one embodiment of small modulation ellipsometer 10 called a polarizer-modulator-sample-analyzer having a light source 12, a polarizer 14, a modulation system 16, a dual analyzer 20 and a harmonic component detector 22. Light from the source 12 passes through the polarizer 14 which produces a linear polarization state. The polarized light passes through the modulation system 16 which alters the polarization state of the light at a high ac frequency.

In one embodiment, the modulation amplitude and thus the magnitude of the change in polarization state is kept sufficiently small to cause the calibration constants to be negligible as determined by the appropriate Jones matrix analysis of the system. In another embodiment, a larger modulation amplitude above one-half radian is used and the calibration errors are calculated on line from the third and fourth order terms of the Fourier series and the data corrected. The modulation need not be over two radians in amplitude and preferably is about one radian. It is selected to provide a good signal to noise ratio.

To obtain signals representing the nature of the surface of a sample 18, the polarized light is caused to interact with the sample 18 such as being reflected from the sample 18 or transmitted through the sample 18. It is shown as being reflected from the sample in FIG. 1. The polarized light is altered in state by the delta and psi of the sample and the altered polarization state is passed through an analyzer, such as a Wollaston prism split analyzer, to separate the orthogonally polarized components of the beam. The orthogonally polarized components of the beam of light are sensed and used to determine delta and psi.

Before converting the beams of light to electrical signals, the beam of light incident on the sample 18 or the beams of light resulting from it at the Wollaston prism split analyzer are phase modulated. The modulation in the preferred embodiment occurs after the beam of light passes through the polarizer 14 and before it engages the sample 18, but the beam may be modulated at any location along its path up to the time it is split in the split analyzer or the beams of light may be synchronously modulated after being split and before being converted to electrical signals. For this purpose, the modulation system 16 includes a modulator controller 24 and a quartz rod 26 or other phase modulator which is vibrated to delay and advance the light waves of two orthogonal polarizations as they pass through it to the sample 18.

In the first embodiment mentioned above, the modulator controller 24 causes vibration of the quartz rod 26 at a relatively high frequency but only through a phase angle somewhere between a fraction of a degree and ten degrees and preferably under five degrees. The exact value is chosen to render the effect of calibration constants caused by nonlinear characteristics of components such as the photodiodes to be negligible. In the other embodiment, the phase angle is at a large value and may be at any value but is preferable between one-half radian and two radians.

To obtain two electrical signals, each representing a different one of the two orthogonal planes of polarization of the light after leaving the sample, the dual analyzer 20 includes a split analyzer 30 and two sensors 32. The split analyzer 30 separates each of the orthogonally polarized components of the beam leaving the sample into a separate one of two beams. One such beam splitter is a Wollaston prism split analyzer 30. The two photodetectors shown at 32 each receive only light in its corresponding orthogonal polarized plane. Each of the photodetectors 32 is connected to a different analog to digital converter within the harmonic component detector 22.

The harmonic component detector 22 includes the computer 34 and an analog to digital converter system 36 which receives outputs from two conductors, each of the two conductors shown as a single line 33 in FIGS. 1 and 2 being electrically connected to a different one of the photoelectric devices in the dual photodetectors 32.

The computer 34 computes the Fourier series using standard program software and may be any suitable type of computer or microprocessor capable of making such a calculation. The A/D board 36 includes two analog to digital converters, each connected to a different one of the two conductors shown as the line 33.

A Fourier expansion of the two signals would result in a signal of the type indicated by equation 1 or equation 2 where the angular frequency is omega, $V_a$ is the signal from one of the photosensors, $V_b$ is a signal from the other photosensor, small t is time and each term represents one harmonic of the harmonic expansion in terms of voltage.

The expansion may be formed by any of several means although in the preferred embodiment a Fourier expansion is obtained using a microprocessor and the program provided hereinafter. Commercial Fourier transform programs that are suitable are available as well. Alternate hardware is available for such a Fourier expansion such as by filtering the different frequency components in separate filters, separating the sine and cosine functions for each frequency by phase detection and gating the functions to an output conductor or using a harmonic coefficient generator in the type described in U.S. Pat. No. 2,752,092. Generally in the first embodiment with less than 10 degrees of modulations only the Fourier coefficients lower than the third order are used but in the embodiment using approximately one radian and at least using a range of between one-half radian and two radian coefficients through the third order or fourth order are used.

In FIG. 2, there is a slight modification of the embodiment of FIG. 1, which is that a quarter wave compensator 15 is inserted between the first polarizer 14 and the modulator 16. This produces circularly polarized light at the modulator 16 and nearly circularly polarized light at the sample 18. The detector outputs have the same form as in the embodiments of FIG. 1.

The amplitudes of the dc and harmonic contributions may be extracted using analog or digital filters, and lock-in amplification or digital Fourier analysis. Psi and delta can be determined in the case of the embodiment of FIG. 1

EQUATION 1

$$Va = Va_0 + Va_1\cos(\Omega t) + Va_2\cos(2\Omega t) + Va_3\cos(3\Omega t) + Va_4\cos(4\Omega t); \text{ and}$$

EQUATION 2

$$Vb = Vb_0 + Vb_1\cos(\Omega t) + Vb_2\cos(2\Omega t) + Vb_3\cos(3\Omega t) + Vb_4\cos(4\Omega t),$$

EQUATION 3

$$M^2 = 8\left(\frac{Va_2 Vb_1}{2Va_2 Vb_1 - Va_0 Vb_1 - Va_1 Vb_0}\right)$$

EQUATION 4

$$M^2 = 8\left(\frac{Va_2 Vb_2}{2Va_2 Vb_2 - Va_0 Vb_2 - Va_2 Vb_0}\right),$$

EQUATION 5

$$\tan(\Delta) = \frac{Va_1 M}{4Va_2},$$

EQUATION 6

$$\tan(\Psi) = \frac{1}{2}(U - \sqrt{U^2 - 4}), \text{ and}$$

EQUATION 7

$$U = -2\cos(\Delta)\left(1 + \frac{[Va_0 - Va_2]M^2}{4Va_2}\right).$$

EQUATION 8

$$\sin(\Delta) = \frac{2Va_2}{Ca\tau M^2}$$

EQUATION 9

$$[\tan(\Psi)]^2 = 1 - \frac{Va_1}{CaM}$$

EQUATION 10

$$M^2 = 8\left(\frac{Va_2 Vb_1}{2Va_2 Vb_1 - Va_0 Vb_1 + Va_1 Vb_0}\right)$$

EQUATION 11

$$Ca = \left(\frac{4Va_2 + Va_1 M + (Va_0 - Va_2)M^2}{2M^2}\right)$$

EQUATION 12

$$\tan(\Delta) = \frac{2Va_1 Vb_1 J_2(M)}{[Va_1 Vb_1 + Va_1 Vb_1]J_1(M)}$$

EQUATION 13

$$\tan(\Psi) = \frac{1}{2}(U - \sqrt{U^2 - 4}),$$

EQUATION 14

$$U = 2\cos(\Delta)\left\{\frac{[J_0(M) + 1][Va2Vb_1 - Va_1 Vb2] + 2[Va_0 Vb_1 - Va_1 Vb_0]J_2(M)}{Va_1 Vb_1 + Va_1 Vb_1}\right\}$$

EQUATION 15

$$Va_1 J_3(M) = -Va_3 J_1(M).$$

EQUATION 16

$$Va_0 = ca(1 + \tau^2 - 2\tau\cos[\Delta]J_0[m'] + 2[-\tau^2 + 1][-\epsilon a + \{J_0(m') + 1\}\epsilon m])$$

EQUATION 17

$$Va_1 = 4ca\tau\sin(\Delta)J_1(m') \square Va_2 = 4ca(-[-\tau^2 + 1]\epsilon m + \tau\cos[\Delta])J_2(m')$$

EQUATION 18

$$Va_3 = -4ca\tau\sin(\Delta)J_3(m') \square Va_4 = -4ca(-[-\tau^2 + 1]\epsilon m + \tau\cos[\Delta])J_4(m')$$

EQUATION 19

$$Vb_0 = cb(2[-\tau^2 + 1][\epsilon a + \{J_0(m') + 1\}\epsilon m] + 2\tau\cos[\Delta]J_0[m'] + \tau^2 + 1)$$

EQUATION 20

$$Vb_1 = -4cb\tau\sin(\Delta)J_1(m')$$

EQUATION 21

$$Vb_2 = 4cb(-[-\tau^2 + 1]\epsilon m - \tau\cos[\Delta])J_2(m')$$

EQUATION 22

$$Vb_3 = 4cb\tau\sin(\Delta)J_3(m')$$

EQUATION 23

$$Vb_4 = 4cb([-\tau^2 + 1]\epsilon m + \tau\cos[\Delta])J_4(m')$$

EQUATION 24

$$\Delta Va_1 J_3(m') = -Va_3 J_1(m')$$

EQUATION 25

$$\Delta Vb_1 J_3(m') = -Vb_3 J_1(m')$$

EQUATION 26

$$\Delta Va_2 J_4(m') = -Va_4 J_2(m')$$

EQUATION 27

$$\Delta Vb_2 J_4(m') = -Vb_4 J_2(m')$$

EQUATION 28

$$\Delta \sin(\Delta) = 2 \frac{\cos(\Delta) Va_1 Vb_1 J_2(m')}{(Va_1 Vb_2 + Va_2 Vb_1) J_1(m')}$$

EQUATION 29

$$\Delta \tau^2 - \tau U + 1 = 0$$

EQUATION 30

$$\Delta \tau = \frac{1}{2}(U + \sqrt{U^2 - 4})$$

EQUATION 31

$$\Delta \tau = \frac{1}{2}(U - \sqrt{U^2 - 4})$$

EQUATION 32

$$U = 2 \frac{\cos(\Delta)[J_0\{m'\} + 1][Va_2 Vb_1 - Va_1 Vb_2] + 2[Va_0 Vb_1 - Va_1 Vb_0]J_2[m']}{Va_1 Vb_2 + Va_2 Vb_1}$$

EQUATION 33

$$\Delta \epsilon m = \frac{\tau \cos(\Delta)(Va_1 Vb_2 - Va_2 Vb_1)}{(1 - \tau^2)(Va_1 Vb_2 + Va_2 Vb_1)}$$

EQUATION 34

$$\Delta \epsilon a = -\frac{\tau \cos(\Delta) \left( 2 \frac{[Va_0 Vb_1 + Va_1 Vb_0]J_2[m']}{Va_1 Vb_2 + Va_2 Vb_1} + J_0[m'] \right)}{1 - \tau^2}$$

23

PROGRAM A proto.cpp

/* This code is written to acquire data with a D50 data acquisition board manufactured by Metrabyte Co.
The code will acquire data from the modulation ellipsometer and convert it to Psi and Delta.
For the executable program to be complete and functional at all this file (proto.cpp) should be linked with d50.cpp and show.cpp.
The code is to be compiled with a Borland C++ compiler or compatible written by *Hassanayn Machlab* June-1992
*/

```cpp
#include<dos.h>
#include<complex.h>
#include<stdio.h>
#include<iostream.h>
#include<string.h>
#include<stdlib.h>
#include<conio.h>
#include<math.h>
#include"has.h"
#include<graphics.h>
extern int D50InputInt(int *Int);
extern void GetError();
extern FILE *D50;
FILE *out;
extern graphinit();
extern void DAS50(void);
extern void plotfourier(float *,int,int,int,int,int);
extern complex *getfourierc(float *rawdata,int);
extern int  D50Output(char *Str);
int fileread(void);
int directread(float *);
float *GetPsiDelta(int,char);
void initD50(void);
void AcquireAndSave(void);
void insitu(void);
int datapts;
int numwaves=1;
float channel0[2030],channel1[2030],DCoffset0,DCoffset1,m=0;
int data[2030];
extern char filename[20];
main()
{    complex *gfcch0,*gfcch1;
     char fileout[20],ch;
```

```
                int channels=0,choice,j=0;
                initD50();
dc:

// get background noise before acquiring data printf("Block the light beam for dc offset measurement...\n");
                printf("push any key to take measurement\n");
                getch();
                directread(channel0);            // read data from channel 0
                gfcch0=getfourierc(channel0,datapts);    // fourier transform the data
                DCoffset0=abs(gfcch0[0]);
                printf(" DCoffset0=%f\n",DCoffset0);
                directread(channel1);            // read data from channel 1
                gfcch1=getfourierc(channel1,datapts);    // fourier transform the data
                DCoffset1=abs(gfcch1[0]);
                printf(" DCoffset1=%f\n",DCoffset1);

printf("\nPush any key to continue acquiring data\n");
                getch();

// start acquiring data
menu:   clrscr();
                printf("DATA ACQUISITION FROM ME\n\n");
                printf("1.acquire data thru interface or read from file\n");
                printf("2.acquire several data and save results to a file\n");
                printf("3.acquire one set of data \n");
                printf("4.display file contents \n");
                printf("5.measure dc offset\n");
                printf("6.insitu\n");
                printf("99. exit\n");
                scanf("%d",&choice);
reask:
                if(!(choice == 99 || choice == 4))
                {
                  printf("enter the number of cycles to average at (max=100)\n");
                  scanf("%d",&numwaves);
                }
                if(numwaves>100)goto reask;

switch(choice)
                {
                case 1:
                  channels=fileread();
                  GetPsiDelta(channels,'0');
```

```
      goto menu;
    case 2:
      printf("enter filename to store the data in\n");
      scanf("%s",fileout);
      out=fopen(fileout,"w+");
      AcquireAndSave();;
      fclose(out);
      goto menu;

case 3:
      if (D50Output("Set Channels=0\n")) GetError();
      directread(channel0);
      if (D50Output("Set Channels=1\n")) GetError();
      directread(channel1);

// plot data
            graphinit();
            plotfourier(channel0,datapts,25,290,25,215);
            plotfourier(channel1,datapts,310,600,25,215);
            wind ch00(40,290,260,450,0,0,0,0);
            ch00.plotreal(channel0,datapts,"channel-0");
            wind ch1(310,600,260,450,0,0,0,0);
            ch1.plotreal(channel1,datapts,"channel-1");
            getch();
            closegraph();
      channels=2;
      GetPsiDelta(channels,'0');
      getch();
      goto menu;

case 4:
      clrscr();
      printf("enter filename to display \n");
      scanf("%s",fileout);
      if((out=fopen(fileout,"r")) == NULL)
      { printf("error opening %s\n",fileout);
        getch();
        goto menu;
      }
      j=1;
      while(fscanf(out,"%c",&ch) != EOF)
      {
      if(ch == '\n')j++;
      if(j == 25)
            {j=1;
```

26

```
            getch();    // display 25 lines at a time
         }
      printf("%c",ch);
      }
      fclose(out);
      getch();
      goto menu;

case 5:
      goto dc;
   case 6:
      printf("enter filename to store the data in\n");
      scanf("%s",fileout);
      out=fopen(fileout,"w+");
        insitu();
      fclose(out);
        goto menu;

case 99:
        printf("\nprogram terminated by user !!\n");
        fclose(D50);
        exit(0);
   default:
        goto menu;
   } return(0);
}

// Read raw data directly from data acquiaition board without using supplied
software int directread(float *channel)
{
      int status,i,bits,channels;
      unsigned int seg,off;
      float fsv;
      char cmd[100];
      rewind(D50);
      if ( D50Output("Clear\n")) GetError();      // Clear the communication
buffer
      if ( D50Output("stop\n")) GetError();

datapts=numwaves*20;
```

27

```c
        sprintf(cmd,"Set Samples=%d\n",datapts+20);
        if (D50Output(cmd)) GetError();

// acquire data if (D50Output("Acquire \n")) GetError();  // Start the Trace
        do {
           if (D50Output("REad Status\n")) GetError();   //Wait for Trace to be
done
           if (D50InputInt(&status)) GetError();
           printf("++++\r");
           }while ((status & 0x18) != 0x18);

// tranfer data to array if (D50Output("SET ADD=4 \n")) GetError();
        sprintf(cmd,"TRAnsfer %u %u
%d\n",FP_SEG(data),FP_OFF(data),datapts);
        if (D50Output(cmd)) GetError();

// convert binary numbers to equivalent voltages if (D50Output("read range\n")) GetError();
        if (D50InputInt(&status)) GetError();
        switch(status)
        { case 0: fsv=2.5; bits=pow(2,11); break;     //bipolar
          case 1: fsv=5;   bits=pow(2,11); break;
          case 2: fsv=10;  bits=pow(2,11); break;
          case 3: fsv=5;   bits=pow(2,12); break;     //unipolar
          case 4: fsv=10;  bits=pow(2,12); break;
        }
        for(i=0;i<datapts;i++)
        {
        channel[i]=-fsv*data[i]/bits; // convert to voltage
        } channels=1;
        return channels;

}

// initialize data acquisition board
```

28

```
void initD50()
{
        D50 = fopen( "$DAS50","r+");            // open DAS50 for output and input
        if ( D50Output("Clear\n")) GetError();   // Clear the communication buffer
        if ( D50Output("stop\n")) GetError();

if (D50Output("Set Channels=0\n")) GetError();
if (D50Output("Set Samples=48\n")) GetError(); // should be in steps of 16
if (D50Output("Set Range= +-10v\n")) GetError();
if (D50Output("Set Trigger Mode=5\n")) GetError();//6- digital negative edge
if (D50Output("Set Start=After\n")) GetError();
if (D50Output("Set Rate= Int 1e6\n")) GetError();
}

//*********insitu*********************
// read data continuosly and store to a file void insitu(void)
{  int channels,parameter,numpoints,j;
   unsigned _delay;
   char ans,title[20];
   float *PARAMS;
reask:
   clrscr();
   printf("Display quantities or graph ('q' or 'g')?\n");
   printf("enter 'e' to exit\n");
   ans=getch();
   printf("enter total number of points to acquire \n");
   scanf("%d",&numpoints);
   printf("\nenter delay between points in milliseconds\n");
   scanf("%u",&_delay);

if(ans=='g')
   {
param:
   clrscr();
   printf("0. graph Delta from channel0\n");
   printf("1. graph Psi from channel0\n");
   printf("2. graph Delta from channel1\n");
   printf("3. graph Psi from channel1\n");
   scanf("%d",&parameter);
```

```
if(parameter == 0)
    {
        strcpy(title,"Delta-channel 0");
        if (D50Output("Set Channels=0\n")) GetError();
    }
if(parameter == 1)
    {
        strcpy(title,"Psi-channel 0");
        if (D50Output("Set Channels=0\n")) GetError();
    }
if(parameter == 2)
    {
        strcpy(title,"Delta-channel 1");
        if (D50Output("Set Channels=1\n")) GetError();
    }
if(parameter == 3)
    {
        strcpy(title,"Psi-channel 1");
        if (D50Output("Set Channels=1\n")) GetError();
    }
if(parameter <0 || parameter >3)goto param;

graphinit();
wind acquire(40,600,40,450,0,0,0,0);
acquire.plotinsitu(numpoints,title,parameter,_delay);   //0->prints Delta
getch();
closegraph();
goto end;
} if(ans=='q')
{
j=0;
while(j<=numpoints)
{
    if (D50Output("Set Channels=0\n")) GetError();
    directread(channel0);
    if (D50Output("Set Channels=1\n")) GetError();
    directread(channel1);

channels=2;
    PARAMS=GetPsiDelta(channels,' ');
printf("%5.2f %5.2f %5.2f %5.2f %6.4f %6.4f %6.4f\n",
PARAMS[0],PARAMS[1],
PARAMS[2],PARAMS[3],PARAMS[5],PARAMS[4],
```

```
                PARAMS[6]);
            fprintf(out,"%5.2f %5.2f %5.2f %5.2f %6.4f %6.4f %6.4f\n",
                PARAMS[0],PARAMS[1],
                PARAMS[2],PARAMS[3],PARAMS[5],PARAMS[4],
                PARAMS[6]);
            delay(_delay);
            j++;
            }
            printf("\n Done!!, push any key to continue \n");
            getch();
            goto end;
        } if(ans=='e')goto end;

if(ans != 'g' && ans != 'q' && ans != 'e')
    goto reask;
    end:;
}

/* reads data from the DA card through directread() and converts them to Psi and
Delta. Then saves data in desired file.
*/

//*********acquireandsave**************
void AcquireAndSave(void)
{   int channels;
    char ch='0',chtemp;
    float inread,*PARAMS;
    clrscr();
    chtemp=ch;
    while(inread != -1)
    {
    printf("\n enter variable reading, enter -1 to quit\n");
    scanf("%f",&inread);
    if(inread != -1)
        {
        clrscr();
            printf("enter channel '0','1'or '2' for 0 & 1\n");
            ch=getch();
            if(ch != '0' && ch!= '1' && ch!= '2')ch=chtemp;
            chtemp=ch;
            if(ch == '0')
            {
```

```
            if (D50Output("Set Channels=0\n")) GetError();
            directread(channel0);
            }
            if(ch == '1')
            {
            if (D50Output("Set Channels=1\n")) GetError();
            directread(channel1);
            }
            if(ch == '2')    // read data from both channels
            {
            if (D50Output("Set Channels=0\n")) GetError();
            directread(channel0);
            if (D50Output("Set Channels=1\n")) GetError();
            directread(channel1);
            channels=2;
            } printf("channel= %c\n",ch);

PARAMS=GetPsiDelta(channels,ch);   // convert to Psi and Delta

/*************** store data in a file************/
        fprintf(out," %c %5.2f %5.2f %5.2f %5.2f %5.2f %6.4f %6.4f %6.4f\n",
        ch,inread,PARAMS[0],PARAMS[1],
        PARAMS[2],PARAMS[3],PARAMS[5],PARAMS[4],
        PARAMS[6]);
        }
    }
}

//********GetPsiDelta*****************
/* This subdirectory converts the raw data to Psi and Delta.
 for this subroutine Channel0,channel1 and datapts have to be declared outside
main
*/
float *GetPsiDelta(int channels,char ch)
{
        complex *gfcch0,*gfcch1;
        double magch0[20],magch1[20],mcalc1,mcalc2,mcalc;
        double va0,va1,va2,va3,va4,vb0,vb1,vb2,vb3,vb4;
        float U,Delta,Tau,Tau2,PARAMS[10],ca,dummy;
```

32

```
        int signva1,signva2,signvb1,signvb2;
        int j;
        char *p,mp[10];
if(ch !=' ')   // for insitu
{
// modulation..m. Used in calculations.
    mp[0]=6;
    printf("\n enter modulation (in waves), default = %6.4f radians\t",m);
    p=cgets(mp);        //if return is pushed m keeps a default value
    printf("\n");
    if(mp[1] != 0)
    {
    m=atof(p);
    m=m*2*3.14159265;      // convert m from waves to rad
    }
}
else
    m=.1*2*3.14159265;      // convert m from waves to rad
PARAMS[5]=m;
/*******************/
/* channel 0    */
/*******************/
        if(channels==2 || channels==1 && ch=='0')
{
// get the fourier coefficints and put them in gfcch0.

gfcch0=getfourierc(channel0,datapts);      // fourier transform the data
        for (j=0;j<5;j++)
        {
        magch0[j]=abs(gfcch0[j]);
          if(ch !=' ')   // for insitu
printf("va[%d] = %lf phase=%lg re=%lg im=%lg\n",j,magch0[j],
        (atan(imag(gfcch0[j])/real(gfcch0[j])))*180/M_PI,real(gfcch0[j]),
        imag(gfcch0[j]));
        }

// find the sign for the first and second harmonics
        signva1=+1; signva2=+1;
    if(real(gfcch0[7])<0)signva1=-1;  // sign of unaveraged va1 coefficient
    if(real(gfcch0[8])<0)signva2=-1;  // sign of unaveraged va2 coefficient /* assign values for clarity. These are the final values of the fourier coefficients
used in the calculations of Psi and Delta */ va0=magch0[0]-DCoffset0;
```

33

```
        va1=magch0[1]*signva1;          va2=magch0[2]*signva2;
        va3=magch0[3]*(-1)*signva1;     va4=magch0[4]*(-1)*signva2;
    if(ch !=' ')   // for insitu
       printf("Va0=%lf",va0);

/*--------------------
results for channel 0
--------------------*/
// Calculation of DELTA Delta=atan(0.25*va1*m/va2);
    if(ch !=' ')   // for insitu
            if(signva1==-1 && signva2==+1)
                printf("\nDelta-a= %f deg\t",(M_PI+Delta)*180/3.14159265);
            else
                printf("\nDelta-a= %f deg\t",Delta*180/3.14159265);

// Calculation of U and Tau

U=0.5*cos(Delta)*((va0*m*m/va2)-m*m+4);   // channel 'a' calculation
            if(U<=-2)U=U*(-1);
        if(ch !=' ')   // for insitu
          printf("U= %f\t",U);
          if(U>=2)
          {
          Tau=-0.5*sqrt(U*U-4)+0.5*U;   // channel 'a' calculation
        if(ch !=' ')   // for insitu
          printf("psi-a= %f\n\n",atan(Tau)*180/M_PI);
          }
          else
          {
          Tau=9999;
        if(ch !=' ')   // for insitu
          printf("Tau is complex\n");
          } if(signva1==-1 && signva2==+1)Delta=M_PI+Delta;
        if(signva1==+1 && signva2==-1)Delta=2*M_PI+Delta;
        if(signva1==-1 && signva2==-1)Delta=M_PI+Delta;

PARAMS[0]=Delta*180/M_PI;  PARAMS[1]=atan(Tau)*180/M_PI;
}
```

```
/***************/
/* channel 1   */
/***************/ if(channels == 2 || channels==1 && ch=='1')
{
        gfcch1=getfourierc(channel1,datapts);      // fourier transform the data
        for (j=0;j<5;j++)
        {
        magch1[j]=abs(gfcch1[j]);
if(ch !=' ')    // for insitu
printf("vb[%d] = %lf phase=%lg re=%lg im=%lg\n",j,magch1[j],
        (atan(imag(gfcch1[j])/real(gfcch1[j])))*180/M_PI,real(gfcch1[j]),
        imag(gfcch1[j]));
        }

// find the sign for the first and second harmonics
        signvb1=+1; signvb2=+1;
        if(real(gfcch1[7])<0)signvb1=-1; // sign of unaveraged vb1
        if(real(gfcch1[8])<0)signvb2=-1; // sign of unaveraged vb2

// assign values for clarity
      vb0=magch1[0]-DCoffset1;
      vb1=magch1[1]*signvb1;           vb2=magch1[2]*signvb2;
      vb3=magch1[3]*(-1)*signvb1;      vb4=magch1[4]*(-1)*signvb2;
    if(ch !=' ')    // for insitu
      printf("Vb0=%lf",vb0);

/*_____
results from channel1
_____*/

// calculation of Delta

Delta=atan(0.25*vb1*m/vb2);
      if(ch !=' ')    // for insitu
        if(signvb1==+1 && signvb2==-1)
           printf("\nDelta-b= %f deg\t",(M_PI+Delta)*180/3.14159265);
        else
           printf("\nDelta-b= %f deg\t",Delta*180/3.14159265);
```

```
// calculation of U and Tau
    U=0.25*cos(Delta)*(-(vb0*m*m/vb2)+m*m-4); // channel 'b' calculation
    if(U<=-1)U=U*(-1);
if(ch !=' ')  // for insitu
    printf("U= %f \t",U);
    if(U>=1)
    {
    Tau=U-sqrt(U*U-1);
if(ch !=' ')  // for insitu
    printf("psi-b= %f\n\n",atan(Tau)*180/M_PI);
    }
    else
    {
    Tau=9999;
if(ch !=' ')  // for insitu
    printf("Tau is complex\n");
    } if(signvb1==+1 && signvb2==-1)Delta=M_PI+Delta;
    if(signvb1==-1 && signvb2==+1)Delta=2*M_PI+Delta;
    if(signvb1==-1 && signvb2==-1)Delta=M_PI+Delta;

/******************************************************/

PARAMS[2]=Delta*180/M_PI;PARAMS[3]=atan(Tau)*180/M_PI;
}
    if(channels ==2)
    {
// // claculation of modulation
    mcalc=8*va2*vb2/(2*va2*vb2-va0*vb2-va2*vb0);
    mcalc1=8*(va2*vb1/(2*va2*vb1-va0*vb1-va1*vb0));
    if(mcalc<0 || mcalc1 <0)
    {
    if(ch !=' ')  // for insitu
    {
    if(mcalc<0)
    printf("\nm calculated from v2's & v0's is a complex number,sqrt(%lf)\n",mcalc);
    if(mcalc1<0)
    printf("\nm calculated from v1's & v2's & v0's is a complex number,sqrt(%lf)\n",mcalc);
    }
    }
    else
    {
```

```
        mcalc=sqrt(mcalc);
    if(ch !=' ')    // for insitu
        {
        printf("m calculated from v2's & v0's m= %lf \n",mcalc/(2*M_PI));
        printf("m calculated from v1's,v2's & v0's m= %lf \n",mcalc1/(2*M_PI));
        }
        PARAMS[4]=mcalc;
        PARAMS[6]=mcalc1;

}
} return PARAMS;

}

/* the following subroutine reads data from files ganerated by the software
supplied with the data acquisition board */ int fileread()
{
    char a[50];
    int numsamples,j,m,e,bits,jj,throwpts,i,channels;
    float fsv,b,dummy,max;
    double rate;
    long pos,mant,expon;
    FILE *in;

reask:
        DAS50();

if((in=fopen(filename,"r+"))==NULL)
        {
        printf("error, couldn't open %s. Push any key to continue\n",filename);
        getch();
        goto reask;
        } a[0]='\0';
while(strcmp(a,"SampleSetSize"))fscanf(in,"%s",&a);
fscanf(in,"%d",&numsamples);
while(strcmp(a,"RateMantissa"))fscanf(in,"%s",&a);
fscanf(in,"%ld",&mant);
```

```c
while(strcmp(a,"RateExponent"))fscanf(in,"%s",&a);
fscanf(in,"%ld",&expon);
while(strcmp(a,"Channels"))fscanf(in,"%s",&a);
fscanf(in,"%d",&channels);
rate=((double)mant*pow(10,(double)expon))*channels;
while(strcmp(a,"Polarity"))fscanf(in,"%s",&a);
fscanf(in,"%s",&a);
if(!(strcmp(a,"Bipolar")))bits=pow(2,11);
if(!(strcmp(a,"Unipolar")))bits=pow(2,12);
while(strcmp(a,"FSMantissa"))fscanf(in,"%s",&a);
fscanf(in,"%d",&m);
while(strcmp(a,"FSExponent"))fscanf(in,"%s",&a);
fscanf(in,"%d",&e);
fsv=m*pow(10,e);   // calculation of full scale voltage clrscr();
printf("enter number of waves\n");

scanf("%d",&numwaves);
datapts=(1/(rate*50e3))*numwaves;
if(numsamples<datapts)
{
printf("not enough number of samples\n");
fclose(in);
exit(0);
} while(strcmp(a,"Data"))fscanf(in,"%s",&a);
graphinit();
     for(j=0;j<4;j++)fscanf(in,"%f",&dummy);
if(channels==1)
{
    for(j=0;j<datapts;j++)
    {
    fscanf(in,"%f",&channel0[j]);
    channel0[j]=-fsv*channel0[j]/bits; // convert to voltage
    } plotfourier(channel0,datapts,25,600,25,215);
```

38

```
wind ch0(40,600,260,450,0,0,0,0);
ch0.plotreal(channel0,datapts,"channel-0");
} if(channels==2)
{ for(j=0;j<datapts;j++)
    {
    fscanf(in,"%f,%f\n",&channel0[j],&channel1[j]);
    channel0[j]=-fsv*channel0[j]/bits; // convert to voltage
    channel1[j]=-fsv*channel1[j]/bits; // convert to voltage
    }
    plotfourier(channel0,datapts,25,290,25,215);
    plotfourier(channel1,datapts,310,600,25,215);
    wind ch00(40,290,260,450,0,0,0,0);
    ch00.plotreal(channel0,datapts,"channel-0");
    wind ch1(310,600,260,450,0,0,0,0);
    ch1.plotreal(channel1,datapts,"channel-1");

}
    fclose(in);
    getch();
    closegraph();
    return channels;
}
```

38

PROGRAM B

Computer code for calculating $\phi$ and $\Delta$ from the Fourier coefficients Using the Bessel Function solutions

Hasanayn Machlab 1995

```
Function J0 (x#) As Double
'CALCULATION OF THE 0-TH ORDER BESSEL FUNCTION TAKEN FROM NUMERICAL RECIPES
        Dim ax, z As Double
        Dim xx, y, ans, ans1, ans2 As Double
    If ((ax = Abs(x)) < 8#) Then
        y = x * x
        ans1 = 57568490574# + y * (-13362590354# + y * (651619640.7 + y * (-11214424.18 + y *
            (77392.33017 + y * (-184.9052456)))))
        ans2 = 57568490411# + y * (1029532985# + y * (9494680.718 + y * (59272.64853 + y *
            (267.8532712 + y * 1#))))
        ans = ans1 / ans2
    Else
        z = 8# / ax
        y = z * z
        xx = ax - .785398164
        ans1 = 1# + y * (-.001098628627 + y * (.00002734510407 + y * (-.000002073370639 + y *
            2.093887211E-07)))
        ans2 = -.01562499995 + y * (.0001430488765 + y * (-.000006911147651 + y * (7.621095161E-
            07 - y * 9.34935152E-08)))
        ans = Sqr(.636619772 / ax) * (Cos(xx) * ans1 - z * Sin(xx) * ans2)
    End If
    J0 = ans
End Function Function J1 (x#) As Double
'CALCULATION OF THE 1-ST ORDER BESSEL FUNCTION TAKEN FROM NUMERICAL RECIPES
        Dim ax, z As Double
        Dim xx, y, ans, ans1, ans2 As Double
    If ((ax = Abs(x)) < 8#) Then
        y = x * x
        ans1 = x * (72362614232# + y * (-7895059235# + y * (242396853.1 + y * (-2972611.439 + y *
            (15704.4826 - y * (30.16036606))))))
        ans2 = 144725228442# + y * (2300535178# + y * (18583304.74 + y * (99447.43394 + y *
            (376.9991397 + y * 1#))))
        ans = ans1 / ans2
    Else
        z = 8# / ax
        y = z * z
        xx = ax - 2.356194491
```

```
            ans1 = 1# + y * (.00183105 + y * (-.00003516396496 + y * (.000002457520174 + y * (-
                    .000000240337019))))
            ans2 = .04687499995 + y * (-.0002002690873 + y * (.0000008449199096 + y * (-
                    .00000088228987 + y * .000000105787412)))
            ans = Sqr(.636619772 / ax) * (Cos(xx) * ans1 - z * Sin(xx) * ans2)
            If (x < 0#) Then ans = -ans
        End If
        J1 = ans
    End Function Function Jn (n%, x#) As Double
    ' CALCULATION OF THE N-TH ORDER BESSEL FUNCTION TAKEN FROM NUMERICAL RECIPES
        Dim j As Integer, jsum As Integer, m As Integer
        Dim bj As Single, bjm As Single, bjp As Single, sum As Single, tox As Single, ans As Single Dim ax As
                Double
        Dim ACC, bigno, bigni
        ACC = 40
        bigno = 10000000000#
        bigni = .0000000001
        If (n < 2) Then
            MsgBox "n can't be less than 2" Jn = 0
            Exit Function
        End If
        ax = Abs(x)
        If (ax = 0) Then
            Jn = 0
            Exit Function
        ElseIf (ax > n) Then
            tox = 2 / ax
            bjm = J0(ax)
            bj = J1(ax)
            For j = 1 To n - 1
                bjp = j * tox * bj - bjm bjm = bj
                bj = bjp
            Next j
            ans = bj
        Else
            tox = 2 / ax
            m = 2 * (n + Int((Sqr(ACC * n) / 2))) jsum = 0
            bjp = ans = sum = 0
            bj = 1
            For j = m To 1 Step -1
                bjm = j * tox * bj - bjp bjp = bj
                bj = bjm
```

```
            If (Abs(bj) > bigno) Then bj = bj * bigni
                bjp = bjp * bigni ans = ans * bigni sum = sum * bigni
            End If
            If (jsum) Then sum = sum + bj jsum = Not jsum
            If (j = n) Then ans = bjp
        Next j
        sum = 2 * sum - bj
        ans = ans / sum
    End If
    If x < 0 And (n Mod 2) = 1 Then
        Jn = -ans
    Else
        Jn = ans
    End If
End Function Function m_bessel (m As Double, ii As Integer) As Double
'CALCULATION OF THE MODULATION AMPLITUDE
    Select Case ii
        Case 113
            m_bessel = v(0, 0, 1) * Jn(3, m) + v(0, 0, 3) * J1(m)
        Case 213
            m_bessel = v(1, 0, 1) * Jn(3, m) + v(1, 0, 3) * J1(m)
        Case 124
            m_bessel = v(0, 0, 2) * Jn(4, m) + v(0, 0, 4) * Jn(2, m)
        Case 224
            m_bessel = v(1, 0, 2) * Jn(4, m) + v(1, 0, 4) * Jn(2, m)
        Case Else
            MsgBox "Error selecting the modulation equation"
    End Select
End Function Function solve () As Double
' SOLVING THE TRANSCENDENTAL EQUATION FOR THE MODULATION AMPLITUDE
    Dim ITMAX As Integer
    ITMAX = 100
    Dim EPS As Double
    EPS = .00000003
' numerical recipes p 268. Brent method. 'float solve(float(*func)(float))
    Dim iter As Integer
    Dim fa, fb, fc, q, p, qu, r, s, tol1, xm, c, d, e, min, min1, min2, tol As Double Dim a As Double
    Dim b As Double
    Dim ii As Integer
```

```
a = -1
b = 5
tol = .00001
' now we decide which function to use to get m. There are 4 possiblities
    If Abs(v(0, 0, 1)) >= Abs(v(0, 0, 2)) Then 'use v1 and v3
        If Abs(v(0, 0, 1)) >= Abs(v(1, 0, 1)) Then
            ii = 113 'use A13
        Else
            ii = 213 'use B13
        End If
    Else
        If Abs(v(0, 0, 2)) >= Abs(v(1, 0, 2)) Then 'use A24
            ii = 124
        Else 'use b24
            ii = 224
        End If
    End If
fa = m_bessel(a, ii)
fb = m_bessel(b, ii)
For iter = 1 To ITMAX
    If (fb * fc > 0#) Then
        c = a
        fc = fa
        e = b - a
        d = e
    End If
    If (Abs(fc) < Abs(fb)) Then
        a = b
        b = c
        c = a
        fa = fb
        fb = fc
        fc = fa
    End If
    tol1 = 2# * EPS * Abs(b) + .5 * tol xm = .5 * (c - b)
    If (Abs(xm) <= tol1 Or fb = 0#) Then solve = Abs(b)
        Exit Function
    End If
    If (Abs(e) >= tol1 And Abs(fa) > Abs(fb)) Then s = fb / fa
        If (a = c) Then
            p = 2# * xm * s
            q = 1# - s
        Else
```

42

43

```
            q = fa / fc
            r = fb / fc
            p = s * (2# * xm * q * (q - r) - (b - a) * (r - 1#)) q = (q - 1#) * (r - 1#) * (s - 1#)
        End If
        If (p > 0) Then
            q = -q
        End If
        p = Abs(p)
        min1 = 3 * xm * q - Abs(tol1 * q)
        min2 = Abs(e * q)
        If min1 < min2 Then min = min1 Else min = min2 'if(2.0*p <(min1 <min2 ? min1 : min2)) then
            If (2# * p) < min Then
                e = d
                d = p / q
            Else
                d = xm
                e = d
            End If
        Else
            d = xm
            e = d
        End If
        a = b
        fa = fb
        If (Abs(d) > tol1) Then
            b = b + d
        Else
            If xm > 0# Then
                b = b + Abs(tol1)
            Else
                b = b - Abs(tol1)
            End If
        End If
        fb = m_bessel(b, ii)
    Next iter
    MsgBox " maximum number of iterations exceeded in root finding "
End Function Sub calcpsidelta ()
    ëCALCULATION OF PSI AND DELTA
    Dim const1 As Double
    Dim const2 As Double
    Dim const3 As Double
```

44

```
    Dim Ubessel As Double
    Dim taubessel As Double
    Dim deltabessel As Double
    Dim signva1, signva2
    Dim u, tau
    Dim psi2
' Delta from the bessel funtions
    modulation = solve()
    const1 = Jn(2, modulation)
    const2 = J1(modulation)
    deltabessel = Atn(2 * v(0, 0, 1) * v(1, 0, 1) * const1 / ((v(0, 0, 1) * v(1, 0, 2) + v(0, 0, 2) * v(1, 0, 1)) *
            const2))
    signva1 = Sgn(v(0, 0, 1))
    signva2 = Sgn(v(0, 0, 2))
    If (signva1 < 0 And signva2 >= 0) Then 'reflection 'first quadrant
        delta = Abs(deltabessel)
    ElseIf (signva1 < 0 And signva2 < 0) Then 'reflection 'second quadrant
        delta = -Abs(deltabessel) + pi
    ElseIf (signva1 >= 0 And signva2 < 0) Then 'reflection 'third quadrant
        delta = Abs(deltabessel) + pi
    ElseIf (signva1 >= 0 And signva2 >= 0) Then 'reflection 'fourth quadrant
        delta = -Abs(deltabessel) + 2 * pi
    End If
    delta = delta * 180 / pi
    Ubessel = 2 * Cos(deltabessel) * ((J0(modulation) + 1) * (-v(0, 0, 1) * v(1, 0, 2) + v(0, 0, 2) * v(1, 0, 1)) +
            2 * (v(0, 0, 0) * v(1, 0, 1) - v(0, 0, 1) * v(1, 0, 0)) * Jn(2, modulation)) / (v(0, 0, 1) * v(1, 0,
            2) + v(0, 0, 2) * v(1, 0, 1))
    u = 1 / 2 * Cos(deltabessel) * ((v(0, 0, 1) * modulation * modulation / v(0, 0, 2)) - modulation *
            modulation + 4)
    tau = 1 / 2 * Sqr(Abs(u * u - 4)) + u / 2
    psi2 = Atn(tau) * 180 / pi
    taubessel = -.5 * Sqr(Abs(Ubessel * Ubessel - 4)) + .5 * Abs(Ubessel)
    psi = Atn(taubessel) * 180 / pi
' CALCULATION OF ANGLE ERRORS
    const1 = v(0, 0, 0) * v(1, 0, 1) + v(0, 0, 1) * v(1, 0, 0)
    const2 = v(0, 0, 1) * v(1, 0, 2) + v(0, 0, 2) * v(1, 0, 1) const3 = v(0, 0, 1) * v(1, 0, 2) - v(0, 0, 2) * v(1, 0, 1)
    epsilonm = taubessel * Cos(deltabessel) * (const3) / ((1 - taubessel ^ 2) * const2)
    epsilonm = epsilonm * 180 / pi
' bessel function solutions
    epsilona = -taubessel * Cos(deltabessel) * (2 * const1 * Jn(2, modulation) + const2 * J0(modulation)) /
            ((1 - taubessel ^ 2) * const2)
    epsilona = epsilona * 180 / pi
End Sub
```

44 for the embodiment in which M is less than 10 degrees from equations 3, 4, 5, 6 and 7 and for the embodiment in which M may be any value but is preferably one radian are determined from equations 12, 13, 14, and one of 15, 24, 25, 26 and 27. In the case of the embodiment of FIGS. 2, for the embodiment in which M is less than ten degrees equations 8, 9, 10 and 11 may be used to determine psi and delta and for the embodiment in which M may be any value but is preferably one radian are determined from equations 12, 13, 14, and one of 15, 24, 25, 26 and 27. In these equations M is the modulation amplitude.

It can be determined from these equations that psi and delta are independent from the calibration errors in the embodiment in which the modulation is less than 10 degrees. As can be determined from a conventional Jones matrix, psi and delta are functions of the sine and cosine of the modulation angle. Thus, for modulation angles that are very small, the sine is so small that the terms containing the sine are negligible and the terms containing the cosine are substantially equal to one. Because of this, for small angles of modulation, the effect caused by misalignment does not affect the end result in any significant way. Generally, the modulation angle which results in independence from alignment errors is less than ten degrees and preferably under five degrees.

The embodiment using M equal to less than 10 degrees incorporates a power series expansion in the polarization modulation (PM) amplitude that limited the practical operation amplitude to 6 degrees (0.1 radian). However, the small modulation produces a low signal-to-noise ratio for the important third and fourth harmonics of the PM frequency and limits the overall prevision of the values of psi and delta.

The embodiment that may use a larger M is based on an analysis which is exact to all orders of the modulation amplitude. The essential harmonic expansion is retained; the values of tau and delta are calculated from the Fourier harmonic expansion of the PM signal. The expressions for the Fourier coefficients are exact to all orders of the modulation signals in the two orthogonal polarizations at the output of the analyzer are readily written as harmonic expansion in the modulation amplitude M are shown in equations 1 and 2. The equations 12-15 and 24-27 are accurate in the presence of misalignment of the sample, modulator, or analyzer about the optical axis, provided that such misalignment is no larger than five degrees for any of these misalignments.

The amplitudes of the dc and harmonic contribution to these signals are extracted by digital Fourier analysis. The values of psi and delta are obtained from equations 12 and 13 where equation 14 defines U. Here $J_v$ (M) is the integer Bessel function of order v and M is obtained from one of the four transcendental equations shown as equations 15 and 24-27. The original small modulation solutions are recovered by expanding the Bessel functions to the fourth power of M.

The calculation of errors in alignment of the modulator (delta epsilon M) and the calculation of errors in the alignment of the analyzer (delta epsilon A) performed by the computer are shown in equations 20 through 34 in step-by-step fashion with $theta_p$ being equal to one-quarter pi, $theta_a$ being equal to epsilon A plus one-quarter sgn pi, $theta_m$ being equal to epsilon M, rho M being equal to one, sgn squared being equal to one, and M being equal to M prime times the cosine (T). Equations 16 through 23 provide the coefficients of the Fourier harmonics. The calculations for the delta and psi are obtained by solving at least one of equations 24 through 27 for imprime, and substituting imprime into equations 28 through 34 to obtain the alignment error of the modulator, the alignment error of the analyzer equations 33 and 34 and delta and psi (tangent of tau) equations 28 through 32. The program for calculating psi and delta using small modulation is shown in program A and the program for solving for tau and psi using larger modulation but correcting alignment errors by calculating the errors from the third or fourth order coefficients of the Fourier series is shown in program B herein.

In FIG. 3, there is shown another embodiment 10A of the ellipsometer substantially the same as the embodiment 10 shown in FIG. 1 except that it incorporates an additional amplitude modulation stage to reduce noise. In embodiment 10A, a source of amplitude modulation signals 46 modulates the source of light 12A, which may be a laser, in intensity so as to provide an intensity modulated light source to the polarizer 14 rather than unmodulated light from the source of light 12 as in the embodiment 10 of FIG. 1. The light signal after passing through the dual analyzer is demodulated before being applied to the analog to digital converter system 36 by being applied to a mixer 42 which is also connected to a function generator or to the source 46 to mix the signals and then being applied to a low pass filter 40 in a demodulator 38. This results in a lower noise signal being applied to the converter.

This amplitude modulation of the light source at a frequency $f_c$, called the carrier frequency, which is larger than the frequency of polarization modulation, when added to the phase modulation, causes all signals to be carried at high frequency, thus reducing noise and, particularly, eliminating dc offset or drift voltages. The original construction and operation of the SME remains as described above in connection with the embodiment of FIG. 1.

In the operation of the embodiment of FIG. 3, the source is amplitude modulated at high frequency. Amplitude modulation can be achieved by direct modulation of a laser source or by use of an external modulator such as an acousto-optic or electro-optic modulator. The amplitude modulated light passes through the polarizer 14 and polarization modulator 26, reflects from or passes through the sample 18, and then passes through the split polarizer.

The orthogonally polarized components of the light beam are converted to electrical signals by the two detectors 32. These signals are composed of the amplitude modulated carrier signal at frequency $f_c$ with sidebands at the polarization modulation frequency and harmonics as well as undesired dc and ac noise and interference.

The electrical signals are demodulated by standard demodulation techniques, such as synchronous (coherent) detection implemented as in FIG. 3. Demodulation retains only those signals at $f_c$ and its sidebands and rejects all signals that are far from $f_c$. This allows the detection of the information carrying signal and the rejection of the noise and dc offset signals. The signals at fc and its side bands are removed by the low pass filter 40. Alternately, the filtering function can be performed digitally after collection of the full, unfiltered signal by the A/D board.

Equations 3 to 11 are correct to second order in the modulation amplitude M. The accuracy of delta and tan. psi may be improved arbitrarily by using higher harmonics of the two signals Va and Vb. Alternate expressions such as shown in equations 3 and 4 for $M^2$ permit accurate calculation of delta and tan. psi when particular terms of the Fourier expansions (e.g. the nth term $Va_n$ or $Vb_n$) have a low signal-to-noise. Preferably delta and tan. psi are calculated to the fourth order although better precision is obtained by higher order calculations (use of more terms of the Fourier expansion).

In the preferred embodiment, the sources 12 or 12A are each a 5 milliwatt diode laser sold as model LAS-200-670-5 by Laser Max, Inc., 207 Tremont St., Rochester, N.Y. 14608, although a monochrometer with a diffraction grating may be used. The polarizer is a glan-laser polarizer, model MGT25S5 and the split analyzer is a prism polarizer, model MW2A-10-20, both of which are sold by Karl Lambrecht, 4204 N Lincoln Ave., Chicago, ILL. 60618. The compensator used in the embodiment of FIG. 2 is a precision quarter wave plate sold under the catalog no. 02WRQ001-670 by Melles Griot, 1770 Kettering Street, Irvine, Calif. 927124-6463. The modulator is a photoelastic phase modulator system sold under model numbers PEM-90 for the system and PEM-90C for the controller, I/FS50 for the head and with AR coatings by Hinds Corp., 5250 N. E. Elam Young Parkway, Hillsboro, Oreg. 97124-6463. The two detectors are silicon photodiodes, model SD100-13-13-022 sold by Silicon Detector Corp., 1240 Avenida Acaso, Camarillo, Calif. 93010 and the analog to digital converter board is an analog to digital data acquisition board for a personal computer sold under the model DAS-50 by Keithly/Metrabyte, 440 Miles Standish Blvd., Taunton, Mass. 02780.

As can be understood from the above description, this ellipsometric technique has several advantages, such as: (1) it can measure a changing environment, such as for example a surface that is in use such as in a space craft or the like; (2) there is less time necessary for calibrating the instrument to different surfaces; (3) changes in alignment and modulation amplitude can be calculated on-line and corrected during operation; (4) a warning signal can be given automatically if alignment is beyond a predetermined limit; and (5) errors can be displayed to users on-line.

Although a preferred embodiment of the invention has been described with some particularity, many modifications and variations in the invention are possible within the light of the above teachings. Therefore, it is to be understood that, within the scope of the appended claims, the invention may be practiced other than as specifically described.

What is claimed is:

1. A method of ellipsometry comprising the steps of:

polarizing a light beam;

applying the polarized light to a sample;

developing signals representing orthogonal planes of polarization from the light after it has interacted with the sample, whereby two polarized light signals are obtained; and calculating constants, psi and delta, of the sample from a Fourier analysis of the two resulting polarized light signals using at least one coefficient of the Fourier series selected from the orders above the second order to correct for calibration errors, wherein a phase modulator phase modulates the light at a value above one-half pi.

2. A method according to claim 1 in which coefficients of the first, second and third orders are used.

3. A method in accordance with claim 1 in which the light beam is amplitude modulated before being transmitted to the sample and the two signals are demodulated to provide noise reducing synchronous demodulation.

4. A method in accordance with claim 1 in which the beam of light is plane polarized.

5. A method in accordance with claim 1 in which the beam of light is circularly polarized.

6. A method in accordance with claim 1 in which the phase modulator modulates light within a range of one-half radian to two radians.

7. Apparatus comprising:

means for polarizing a light beam;

means for applying the polarized light to a sample;

means for developing signals representing orthogonal planes of polarization from the light after it has interacted with the sample, whereby two polarized light signals are obtained; and means for calculating constants, psi and delta, of the sample from the two resulting polarized light signals, wherein a phase modulator phase modulates the light;

means for expanding the two signals by Fourier analysis and using the coefficients including at least a coefficient above the second order thereof to calculate psi and delta.

8. Apparatus in accordance with claim 7 further including means for amplitude modulating the beam of light before transmitting it to the sample and demodulating the two signals to provide noise reducing synchronous demodulation.

9. Apparatus in accordance with claim 7 further including means for plane polarizing the beam of light.

10. Apparatus in accordance with claim 7 further including means for circularly polarizing the beam of light.

* * * * *